United States Patent
Chattopadhyay et al.

(10) Patent No.: US 11,213,827 B2
(45) Date of Patent: Jan. 4, 2022

(54) DEVICE WITH INTEGRATED METHODS FOR REVERSE TRANSCRIPTION POLYMERASE CHAIN REACTION (RT-PCR) AND/OR DNA/PROTEIN ARRAY BASED ANALYSES

(71) Applicant: INDIAN INSTITUTE OF TECHNOLOGY GUWAHATI, Assam (IN)

(72) Inventors: Arun Chattopadhyay, Assam (IN); Sunil Kumar Sailapu, Assam (IN); Deepanjalee Dutta, Assam (IN); Amaresh Kumar Sahoo, Assam (IN); Siddhartha Sankar Ghosh, Assam (IN)

(73) Assignee: Indian Institute of Technology Guwahati, Guwahati (IN)

( * ) Notice: Subject to any disclaimer, the term of this patent is extended or adjusted under 35 U.S.C. 154(b) by 664 days.

(21) Appl. No.: 15/778,145

(22) PCT Filed: Jun. 2, 2016

(86) PCT No.: PCT/IN2016/000141
§ 371 (c)(1),
(2) Date: May 22, 2018

(87) PCT Pub. No.: WO2017/098521
PCT Pub. Date: Jun. 15, 2017

(65) Prior Publication Data
US 2019/0046988 A1    Feb. 14, 2019

(30) Foreign Application Priority Data

Dec. 9, 2015    (IN) .......................... 1259/KOL/2015

(51) Int. Cl.
| | | |
|---|---|---|
| *B01L 7/00* | (2006.01) | |
| *G01N 33/68* | (2006.01) | |
| *B01L 3/00* | (2006.01) | |

(52) U.S. Cl.
CPC ............. *B01L 7/52* (2013.01); *B01L 3/50857* (2013.01); *G01N 33/68* (2013.01);
(Continued)

(58) Field of Classification Search
None
See application file for complete search history.

(56) References Cited

U.S. PATENT DOCUMENTS

2001/0029017 A1* 10/2001 Yasuda ..................... B01L 7/52
                                                              435/6.11
2012/0295249 A1* 11/2012 Cherubini ............ G01N 35/028
                                                              435/5
(Continued)

*Primary Examiner* — William H. Beisner
(74) *Attorney, Agent, or Firm* — Neifeld IP Law

(57) ABSTRACT

A device with integrated methods for carrying out reverse transcription polymerase chain reaction (RT-PCR) and/or array based analysis involving signal generating agents (gold nanoclusters) comprising a heating and cooling cycle based synthesis selectively with DIMA and protein as templates. The advancement is further directed to a portable device adapted for RT-PCR and array based gene and protein expression analyses based on a common detection agent involving luminescence of in-situ synthesized gold nanoclusters with adaptability for user friendly graphical user interface (GUI) for controlling, visualization and analysis of the data.

3 Claims, 11 Drawing Sheets
Specification includes a Sequence Listing.

(52) U.S. Cl.
CPC ............... *B01L 3/502715* (2013.01); *B01L 2300/027* (2013.01); *B01L 2300/1822* (2013.01)

(56) References Cited

U.S. PATENT DOCUMENTS

2012/0308990 A1* 12/2012 TerMaat .................... B01L 7/52
435/3
2013/0288916 A1* 10/2013 Alexandre ........... C12Q 1/6876
506/9

\* cited by examiner

DEVICE WITH INTEGRATED METHODS FOR REVERSE TRANSCRIPTION POLYMERASE CHAIN REACTION (RT-PCR) AND/OR DNA/PROTEIN ARRAY BASED ANALYSES

CROSS REFERENCE TO RELATED APPLICATIONS

This application is a 371 National Stage Entry of PCT/IN2016/000141 filed Jun. 2, 2016, and PCT/IN2016/000141 claims priority to Indian Application 1259/KOL/2015, filed Dec. 9, 2015. The contents of PCT/IN2016/000141 filed Jun. 2, 2016, is incorporated by reference in its entirety.

REFERENCE TO AN ELECTRONIC SEQUENCE LISTING

The contents of the electronic sequence listing (Sequence-listing_ANJA0019-1_10-25-2018.txt; Size: 4 KB; and Date of Creation: on or about Oct. 25, 2018) is herein incorporated by reference in its entirety.

FIELD OF INVENTION

The invention is related to a device with integrated methods for carrying out reverse transcription polymerase chain reaction (RT-PCR) and/or DNA/Protein array based analyses and, more specifically, to a simple and convenient to use portable device comprising a thermocycler cum visualizing unit enabling to carry out reverse transcription polymerase chain reaction (RT-PCR), end product PCR quantification, array based DNA and protein expression analyses in a single device under effective visualization of reverse transcription polymerase chain reaction end products or array based membranes. Advantageously, the portable device would further favour carrying out studies on genomics and proteomics in a robust and simple way without need for use of any known carcinogen, expensive chemicals and cumbersome synthesis of probing molecules.

BACKGROUND OF INVENTION

Cellular signalling and the related sequence of events directing the response of living cells are governed by a highly sophisticated and regulated pattern of gene expression which can be achieved either at mRNA or protein level. Various technological advancements resulted in the developments of genomics and importantly proteomics, which revolutionized the study of cellular processes. For instance, polymerase chain reaction (PCR) [H. D. Van Guilder et. al., BioTechniques 2008, 44, 619; U.S. Pat. No. 4,683,195] and Microarray (A. L. Beaudet, *Annu. Rev. Med.* 2008, 59, 113; D. S. Wilson et. al. *Angew, Chem. Int. Ed. Engl.* 2003, 42, 494) are widely employed on a large scale for gene expression studies.

It is known that mRNA, being unstable, is usually converted to cDNA by reverse transcriptase enzyme. Then, genes of interest are amplified by using cDNA as template to estimate or compare a particular target to a reference (housekeeping gene) by PCR. There are many variants of this approach. In one type of assays, the end-amplified product of the reference and target gene is analysed by agarose gel matrix followed by ethidium bromide staining. Another revolutionary technique, coined real time PCR, not only amplifies the target and reference sequences but also allows simultaneous detection and quantification during amplification. Usually, a fluorescent probe is added, to the PCR reaction mixture before amplification is carried out, the emission intensity of which increases proportionally with the amount of amplicon. During the amplification, the samples are excited with suitable wavelength of light and the fluorescence output of the samples are measured at different time intervals. The conventional PCR technique facilitates measurement of only a handful number of genes at a time, which makes it difficult to analyse the whole genome of the organism.

Microarray technique facilitated scientists to study thousands of genes simultaneously. For sequencing of mRNA, DNA, drug discovery, pathway studies and genotyping, microarray technology had been predominantly used. DNA microarray based technique is primarily based on hybridization of probe and target DNA (A. A. Gibriel, *Brief Funct. Genomics* 2012, 11, 311). Protein microarray is a high throughput array based approach for study of multiple proteins. However, protein microarray technology is not simple largely due to structural diversity of proteins (3D) originating from post-translational modifications. Further, unknown binding interactions, limited and diverse concentrations, degradation of sample, specificity, drug and disease perturbations induce major hurdles for this technology (M. F. Templin et. al. *Trends Biotechnol.* 2002, 20, 160; V. Espina et. al. *J. Immunol. Methods* 2004, 290, 121). In a broad sense, protein microarrays are patterned with very small amounts of known specific molecules (homogeneous or heterogeneous). These known molecules (may be antibody, a cell or phage lysate, peptide, drug, nucleic acid etc.) must be pure, fairly concentrated and should be in their native form. Usually, a probe or any unknown biological sample immobilizes on to the specific known molecules in the array. The probe molecules contain signal generating agent the signal of which is captured and analysed.

Though PCR and microarray techniques had brought revolutionary changes in the studies of genomics and proteomics, there are certain shortcomings in these techniques as they involve complicated steps, sophisticated instrumentation, trained individuals and high cost factor. Microarrays are often combined with the PCR technology for acquiring the sufficient amount of either the probe and target cDNA. Also, in other cases PCR is often used to complement the results from microarray to focus the study on specific gene sequences (H. Cho, et al *Chem. Commun.* 2012, 48, 7601). The resources employed are expensive and generally not environmentally friendly; Dye like ethidium bromide used for identifying the end product in PCR is known to be carcinogenic and needs special care for its usage and discharge. In real time PCR and microarrays, probes employed are costly and sometimes need designing of sequence specific oligonucleotide dye conjugates necessary for preparation of dye-probe conjugates in order to achieve stable interactions with optimum signal (J. B. Randolph et. al. *Nucleic Acids Res.* 1997, 25, 2923). These molecular fluorophores even exhibit photo-bleaching, photo-blinking thus lowering the efficiency of signal detection. Conventional fluorophores usually require additional modifications to make them water-soluble or increase solubility (B. G. Moreira. *Biophys. Chem.* 2015, 198, 36; M. E. Sanborn *J. Phys. Chem. B* 2007, 111, 11064).

Most of the traditional techniques employed so far require the need for labelling of the probe before interaction with its target analyte, which may affect the stability of the probe thus lowering the efficacy of interactions. In other approaches, radioactive labels are employed which may cause hazardous nuclear waste accumulations (V. Espina et.

al. *J. Immunol. Methods* 2004, 290, 121). Conventional microarray techniques employ several pre and post processing methods. Often, the case of interest is not to examine the complete genome but only some genes of interest (L. Quijada et. al., *Exp. Parasitol.* 2005, 111, 64). But they still require the need to employ complex fabrication procedure used for the entire chip. This makes the analysis difficult in geographical locations where advanced facilities are unavailable.

Nanomaterials are known to enhance thermal efficiency, specificity of interactions, catalytic property and possess the ability to adsorb biomolecules on their surfaces. Based on these properties the applications of nanomaterials in the field of genomics and proteomics (M. R. Mohamadiet.al. *Nano Today* 2006, 1, 38; US 2012/0244075 A1) are featured in several methods to enhance the efficacy of the existing techniques in PCR and microarray based techniques. Nanoparticles, quantum dots, carbon nanotubes, carbon nanopowder, graphene etc., are some of the materials which are shown to improve the efficacy of PCR process (X. Lou, et. al. *Mater. Interfaces* 2013, 5, 6276; F. Sang et al, *J Biomed. Sci. Eng.* 2012, 05, 295). Attempts for the quantification of PCR product have been made by exploiting the plasmonic properties of nanomaterials (M. A. Cai et.al. *Nano Research* 2010, 3, 557). Plasmonic property of the gold nanoparticles have been exploited in the colorimetric detection of biomarker samples in microarrays (D. Kim. Et al. *Anal. Chem.* 2009, 81, 9183). Owing to several advantages over conventional organic dyes/probes, quantum dots have been used as fluorometric probes in analyses involving gene and protein expression studies (R. Q. Liang *Nucleic Acids Res.* 2005, 33, e17).

A class of nanomaterials called nanoclusters is a potential option as a fluorophore for probing gene and protein expression. These nanoclusters (especially the noble metal ones) are ultra-small and comprises of few atoms, highly photostable, low in photo-blinking, non-toxic, bio-friendly and non-carcinogenic, which give them edge over plasmonic nanoparticles, conventional organic fluorophores and quantum dots (X. Yuan. *ACS Nano* 2011, 5, 8800). The nanoclusters being in the lowest dimensions (quantum domain), interact with building blocks of biomolecules such as DNA/protein. A recent report demonstrated usage of BSA stabilized gold nanocluster conjugated to antibody for immune sensing (H. Liu et.al. 3. *Phys. Chem. C* 2012, 116, 2548).

However, there lies a challenge to devise a unique method for easy and rapid synthesis of these signalling agents after the desired biological interactions using the biomolecule itself as the template. This approach would ensure efficient interactions, of the participating blomolecules since synthesis is carried out on the template after the particular interaction has happened. This would also eliminate the extra labour and time invested for separate synthesis or surface modifications or tagging before/after the interactions/amplification as adopted in many other procedures. In this regard, paper based methods are of great interest as they are less expensive, easy to handle, flexible, easily disposable, widely available and can easily be adopted in the field of medical diagnostics (M. N. Costa et. al. *Nanot* 2014, 25, 094006; D. D. Liana et. al. *Sensors (Basel)* 2012, 12, 11505). Particularly, in gene and protein expression studies, nitrocellulose and PVDF (polyvinylidene difluoride) membranes are extensively used due to their charged nature and compatibility with chemical and biomolecules. These stable membranes with uniform pore size are suitable to construct a portable device such as sensors for on-site diagnostics.

In order to overcome the challenges of the existing methods and to facilitate the study of genomics and proteomics there is thus need for low cost, simple, user and bio-friendly technique with simpler instrumentation that would allow accurate and sensitive diagnostics.

OBJECTS OF THE INVENTION

It is thus the basic object of the present invention to provide a device for carrying out reverse transcription polymerase chain reaction (RT-PCR) and/or array based analyses in single unit without requiring separate multiple devices, laborious and time consuming procedures which is highly desired and challenging in the related art as discussed hereinbefore.

Another object of the present invention is to provide a common device for carrying out reverse transcription polymerase chain reaction (RT-PCR) and/or array based analyses involving heating and cooling cycles of the thermocycler for in-situ synthesis of signal generating luminescent agents for effective visualization of reverse transcription polymerase chain reaction end products or array based membranes.

Yet another object of the present invention is to provide a method for carrying out reverse transcription polymerase chain reaction (RT-PCR) and/or array based analyses through visualization involving in situ signal generating luminescent agent for both PCR and array based techniques.

A further object of the present invention is to provide a method of visualization involving in situ signal generating luminescent agent for both PCR and array based techniques involving luminescence intensity of the gold nanoclusters as the signal generating agent which increases monotonically with the concentration of dsDNA or amount of protein.

Another object of the present invention is to provide a method for PCR and array based techniques which would be bio-friendly, non-carcinogenic and involve minimum concentration of precursors and with selective involvement of gold nanoclusters as highly photostable and exhibiting luminescence emission in both liquid phase and in the solid phase.

A further object of the present invention is to provide a method comprising array based technique to study the relative expressions of multiple genes/proteins at a time.

Yet another object of the present invention is to provide a method for PCR and array based techniques free of any required separate synthesis of signal generating agents (clusters), surface modifications and requirement of specific probing molecules.

SUMMARY OF THE INVENTION

Thus according to basic aspect of the present invention, there is provided a device for carrying out reverse transcription polymerase chain reaction (RT-PCR) and/or array based analyses comprising:

a sample carrier selectively for holding PCR tubes and stage for supporting membranes for array based detections;

means for heating and cooling cycles for the sample supported on any said sample carrier;

means for visualization of reverse transcription polymerase chain reacted end products or array based membrane for signal generating luminescent agents based analyses;

said means for visualization comprising light source and imaging.

According to another aspect of the present invention, there is provided a device for carrying out reverse transcription polymerase chain reaction (RT-PCR) and/or array based, analyses comprising:

a sample carrier selectively for holding PCR tubes and stage for supporting membranes for array based detections;

means for heating and cooling cycles for the sample supported on any said sample carrier;

and for in-situ synthesis of signal generating luminescent agents required for effective visualization of reverse transcription polymerase chain reacted end products or array based membranes;

visualization means comprising light source and imaging.

According to another aspect, the present invention provides a device comprising:

i) a thermocycler unit comprising:

said sample carrier selectively for holding PCR tubes and stage for supporting membranes for array based detections;

said means for heating and cooling cycles for the sample supported on any said sample, carrier;

said means for heating and cooling cycle of the sample providing for in-situ synthesis of signal generating luminescent agents for effective visualization of reverse transcription polymerase chain reacted end products or array based membrane; and ii) visualization unit comprising:

UV light source to give source of illumination; and camera to capture the images.

said thermocycler unit and visualization unit interfaced to computer means preferably through programmatically developed GUIs.

In a further aspect, the present invention provides a device wherein said sample carrier comprises (a) a PCR Tube carrier block with at least 7 holes to hold the PCR tubes and temperature sensor and (b) a stage for supporting membrane for said array based analyses;

said means for heating and cooling cycles for the sample comprises (a) heating/cooling element with fan and heat sink to heat/cool the PCR Tube, carrier block along with lid with heating element, temperature sensors for monitoring temperatures of the carrier block and top heating of PCR tubes and (b) means for the heating and cooling of said stage for supporting membrane;

said visualization means comprises UV light source to give source of illumination and web-camera to capture the images.

Yet another aspect of the present invention provides a device wherein said sample carrier with said heating means is adapted to attain temperatures ranging from 15° C. to 95° C., said lid with heating element adapted to attain temperature between room temperature and 120° c.

A further aspect of the present invention provides a device comprising a GUI based control of thermocycler for input parameters including the process (PCR/Array Based Analyses/Custom experiment), phases of operation, temperature parameters, lid control (ON/OFF), lid temperature, start/stop the process and generating the current status and temperature of the sample block and lid;

further GUI for said visualization unit enabling Acquisition, Analysis and generating Reports;

said acquisition enabling acquiring the image, controlling the mode of image and controlling the camera settings;

said acquiring enabling the user to apply a threshold to the image, select and view region of interest (ROI), visualize 3D view of the image, acquire histogram data, perform region and line profile analysis; and said reporting enabling generating the summary of all the selected ROIs, export the data, perform fitting analysis and help estimate amount of the sample using linear regression techniques.

In another aspect, the present invention provides a method for carrying out reverse transcription polymerase chain reaction (RT-PCR) and/or array, based analyses through visualization involving the device comprising:

carrying out in said thermocycler under controlled heating and cooling cycles anyone of (i) subjecting the gene with desired primers for amplification as PCR product (dsDNA) in said PCR tube holder and (ii) membrane based hybridization with complementary ssDNA for array based gene expression studies or incubation with antigen/antibody for array based protein expression studies;

carrying out in-situ synthesis of said signal generating luminescent agents on any one of said (a) thus obtained PCR product (b) hybridized product or incubated protein (interacted antigen—antibody) product on membrane of step (ii) above;

carrying out ready visualization in said visualization unit of said luminescent agents tagged anyone or more of (a) PCR product (b) hybridized product or incubated protein (interacted antigen-antibody) product on membrane to thereby deduce results for the reverse transcription polymerase chain reaction (RT-PCR) and/or array based analyses.

In yet another aspect, the present invention provides a method wherein said step of subjecting the gene with desired primers for amplification as PCR product in said PCR tube holder comprises the steps of:

conversion of the isolated mRNA into cDNA by reverse transcriptase in the thermocycler by heating at 42° C. for 40 min followed by subsequent heating at 95° C. for 2 min; amplification of specific cDNA using desired primers and 2× PCR master mix under controlled heating and cooling cycles in the thermocycler.

carrying out in-situ synthesis of said signal generating luminescent agents comprises synthesizing gold nanoclusters on thus obtained PCR product proportionately to the amplification.

Another aspect of the present invention provides a method comprising:

providing said hybridized product comprises steps of (i) providing membrane with ssDNA; and (ii) hybridizing the said membrane with complementary target ssDNA, said step of carrying out in-situ synthesis of said signal generating luminescent agents comprises synthesizing gold nanoclusters on said hybridised product;

said step of ready visualization in said visualization unit comprises visualizing the gold nanoclusters on said hybridised product and capturing image and quantification of gene expression.

In another aspect of the present invention is provided for a method comprising hybridizing the said membrane with complementary target ssDNA wherein said complementary target ssDNA is obtained from (i) conversion of mRNA to cDNA if available in sufficient concentration or (ii) subjecting the conversion of mRNA to cDNA followed by amplification of desired gene by gene specific primers through PCR if not available in sufficient concentration and involving said amplification product of PCR for said hybridization.

In a further aspect, the present invention provides a method comprising carrying out array based analyses through visualization for array based protein expression studies comprising:

providing the membrane;

blotting primary antibody/antigen on the membrane;

incubating the membrane with antigen/antibody;

carrying out in-situ synthesis of said signal generating luminescent agents comprising synthesizing gold nanoclusters on said membrane thus incubated with antigen/antibody;

ready visualization in said visualization unit comprises visualizing the gold nanoclusters on said membrane thus incubated with antigen/antibody and capturing image and quantification of protein expression.

In yet another aspect, the present invention provides a method wherein said synthesis of gold nanoclusters involve $HAuCl_4$ solution and 3-mercaptopropionic acid.

A further aspect of the present invention provides a method which is bio-friendly, non-carcinogenic and requires minimum concentration of precursors and wherein the gold nanoclusters are highly photostable and exhibit luminescence emission ($\lambda_{em}$=580 nm) when excited at $\lambda_{ex}$=254 nm (254 nm light was used for excitation in the device, 300 nm was used for spectroscopic studies), the luminescence intensity of the gold clusters increases monotonically with the concentration of dsDNA or amount of protein.

A further aspect of the present invention provides a method for relative DNA/protein quantification based on luminescence intensity, devoid of conventional fluorophores (dyes/probes).

Yet another aspect of the present invention provides a method free of any required initial separate synthesis of signal generating agents (clusters), surface modifications and requirement of specific oligonucleotides and wherein synthesis of Au NCs can directly be carried out on DNA itself.

In another aspect, the present invention provides a method comprising a paper based array technique for gene expression studies involving hybridization on nitrocellulose membrane with gold nanoclusters as signal generation agents, involving effectively the less luminescence intensity of gold clusters in ssDNA when compared to dsDNA.

In a further aspect, the present invention provides a method free of any required initial tagging of signal generating agent (fluorophores, optical probes, radioactive labels etc.), separate synthesis of probing molecules.

In yet another aspect, the present invention provides a method comprising array based technique to study the relative expressions of multiple genes at a time.

Another aspect of the present invention provides a method wherein said array based method includes analysis of apoptosis pathway of cells by studying the expression of three genes namely Caspase 3, BCL 2, BAX with respect to (β-actin as control).

A further aspect of the present invention provides a method for relative protein quantification based on luminescence intensity without the use of conventional fluorophores (dyes/probes) and no initial separate synthesis of clusters, surface modifications.

Another aspect of the present invention provides a method comprising a paper based array technique for protein expression studies involving antibody-antigen interaction on PVDF membrane with gold nanoclusters as signal generation agents involving the observation that in the solid phase, intensity of emission from the clusters formed is less in antigen or antibody when compared to interacted antigen-antibody in relation to the amount of protein present.

In another aspect, the present invention provides a method free of any initial tagging of signal generating agent (fluorophores, optical probes, radioactive labels, enzymatic labels etc.) or separate synthesis of probing molecules.

In another aspect, the present invention provides a method wherein the array based method comprises a direct labelling method and requires no secondary antibody for detection.

In a further aspect, the present invention provides a method wherein the array based method facilitates the study of expression of multiple proteins at a time.

Another aspect of the present invention provides a method comprising an array based method wherein GST (glutathione S-transferase) antibody was immobilized and corresponding GST tagged antigens were allowed to interact and wherein the amount of GST tagged antigens can be relatively quantified from the luminescence intensity of the synthesized gold nanoclusters.

A further aspect of the present invention provides a method for enhancing the luminescence intensity of the gold nanoclusters involving zinc ions for signal amplification in case of low intensity levels in solid phase when excited with 254 nm light.

In yet another aspect, the present invention provides a device which is robust, portable and easy to handle.

According to another aspect of the present invention there is provided a method for carrying out reverse transcription polymerase chain reaction (RT-PCR) and/or array, based analyses, the step of generating signal generating agents (clusters) comprising a heating and cooling cycle based synthesis selectively with DNA and protein as templates.

According to a preferred aspect in the above method said heating and cooling cycle based synthesis involves PCR heating and cooling cycles. According to yet further aspect in the above method said heating and cooling cycle based synthesis involves synthesis of gold nanoclusters.

DETAILED DESCRIPTION OF THE INVENTION

The present invention thus provides a portable, easy to handle device and a method for carrying out reverse transcription polymerase chain reaction (RT-PCR) and/or array based analyses using in situ generated signal generating luminescent agents developed in both liquid and solid phases (Liquid phase—reverse transcription of mRNA, amplification of DNA, synthesis of signal generating agents; Solid phase—synthesis of signal generating agents, performing relative gene and protein expression level studies). The device is based on a modular approach so that its different parts are accessed independently.

The device comprises of:
1. Thermocycler Unit which facilitates, to achieve temperatures between 15° C. and 95° C. to heat/cool the sample comprises:
   a. Fan for cooling
   b. Peltier for heating and cooling the holder
   c. Switchable holder with holders suitable for PCR process and array based analyses equipped with temperature sensors
   d. Lid with heating element (cartridge heating element) and temperature sensor
2. Visualization Unit which allows capturing the image under proper excitation and further to carry out analysis comprises:
   a. UV Illumination Source with switchable lamps (Long wavelength, Short wavelength and Mid wavelength; battery powered)
   b. Camera with controllable attributes from GUI
3. Computer/Laptop to run the GUI (Graphical User Interface)s for the thermocycler and the visualization unit.
4. Electronic circuitry which consists of the Arduino Uno Interface Board to execute various operations and additional circuitry.
5. Power Supply Unit.

The additional circuit needed for the, thermocycler is designed and mounted on the Arduino Uno board. However, the microcontroller unit is controlled through a Graphical User Interface. The complete unit can be run with a power source capable of supplying 12 V and 10 A. The Graphical User Interface (GUI) for the thermocycler unit and visualization unit is developed using LabVIEW platform.

Present invention thus relates to an effective method for studying relative gene and protein expression using a common in-situ generated signal generating luminescent agents without the use of costly equipment, carcinogenic materials and synthesis of specific probing molecules.

The common signal generating luminescent agents of the present invention are preferably gold nanoclusters which are highly photostable and are directly synthesized on the PCR products/hybridized spots/proteins in the device. The method for synthesis of gold nanoclusters get easily embedded into the traditional temperature cycling process (also within the temperature limits) of PCR and hence need no external preparation with separate experimental conditions as in case of traditional dyes/other nanomaterials used as signal generating agents. The conditions involving synthesis of gold nanoclusters not only carries out the synthesis but aids further in hybridization. Since the signal generating agents is same for either RT-PCR or DNA/protein array, a single UV excitation is sufficient. These nanoclusters being homogeneous do not need further surface modifications.

The gold nanoclusters emit light at 580 nm when excited at 254 nm in the liquid phase (254 nm light was used as the source for obtaining emission in device, 300 nm light was used for spectroscopic studies). It was observed that the luminescence intensity of the gold clusters increased monotonically with the increase in the concentration of dsDNA/protein. Hence, this would enable differentiation of concentration of DNA/proteins from the intensity of the clusters.

Importantly, this behaviour of luminescence is used to study protein expression, where, with specific antigen-antibody interactions, the relative luminescence changes signifying the extent of interactions. The same is also useful to study gene expression in apoptosis mediated cell death where expression of three apoptotic pathway regulating genes BCL-2 (B-cell lymphoma 2), BAX (BCL2-associated X protein) and Caspase 3 was studied in vitro.

The luminescence intensity of the gold nanoclusters can be enhanced with the interaction of zinc ions. In the case of array based techniques involving both DNA and protein, addition of optimum amount of zinc ions leads to increase in the signal intensity if it is below the detectable limit without altering the results.

Detailed description for each section and the functional attributes are discussed by way of examples hereunder.

A) Gray Scale image under UV illumination showing increasing amounts (left to right in each row as indicated by the arrow) of commercially obtained ssDNA (β-actin) immobilized (spotted) on the nitrocellulose membrane in two rows ((i) 0.18 µg, (ii) 0.37 µg and (iii) 0.74 µg) and different amounts of complementary target ssDNA (commercially obtained) hybridized in the second row ((i) 0.18 µg, (ii) 0.37 µg and (iii) 0.74 µg) with gold nanoclusters synthesized on them. B) The relative luminescence intensity of the gold nanoclusters for increasing amounts of ssDNA and dsDNA.

Figure 11:
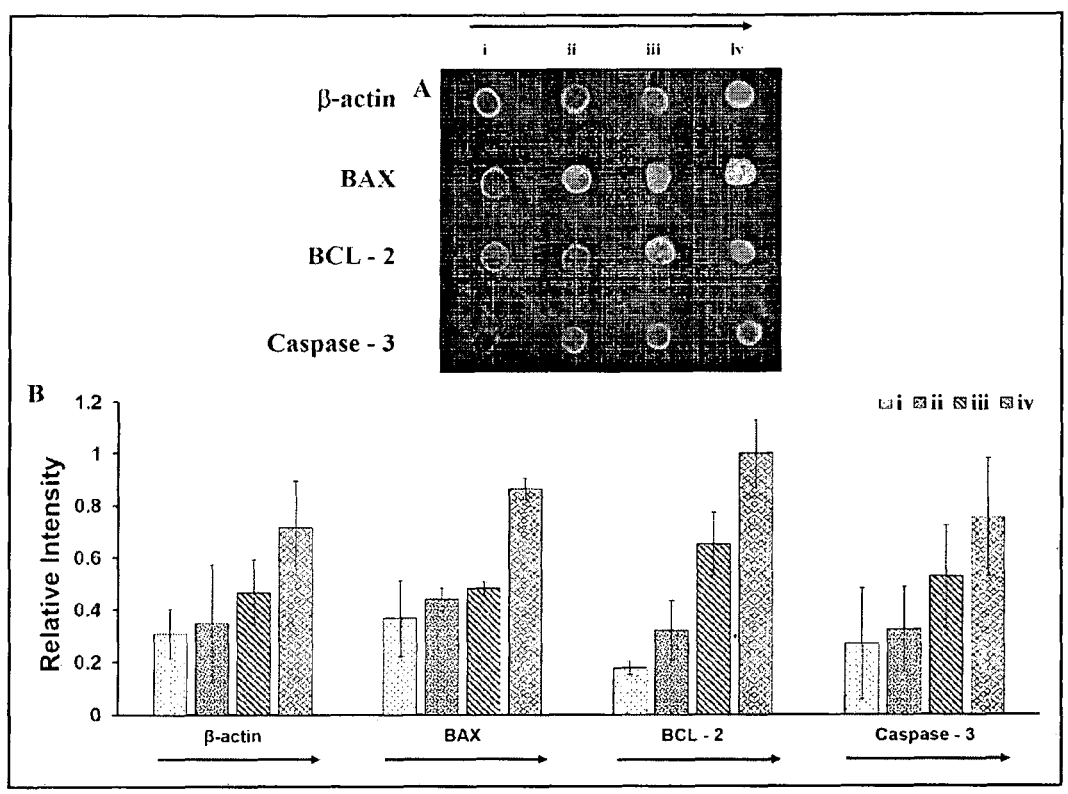

FIG. 11 represents luminescence intensity of gold nanoclusters synthesized in commercially obtained gene sequences immobilized on nitrocellulose membrane.

A) Gray Scale image of the array in the membrane under UV illumination showing increasing amounts (left to right in each row as indicated by the arrow) of commercially obtained ssDNA sequences of β-actin, BCL 2, BAX and Caspase 3 immobilized in each row on the nitrocellulose membrane, respectively ((i) 0.18 µg, (ii) 0.37 µg, (iii) 0.74 µg and (iv) 1.1 µg) and increasing amounts of the complementary target ssDNA were hybridized ((i) 0.18 µg, (ii) 0.37 µg, (iii) 0.74 µg and (iv) 1.1 µg) with gold nanoclusters synthesized on them B) The relative luminescence intensity of the gold nanoclusters with increasing amounts of hybridized DNA for various genes.

Figure 12:
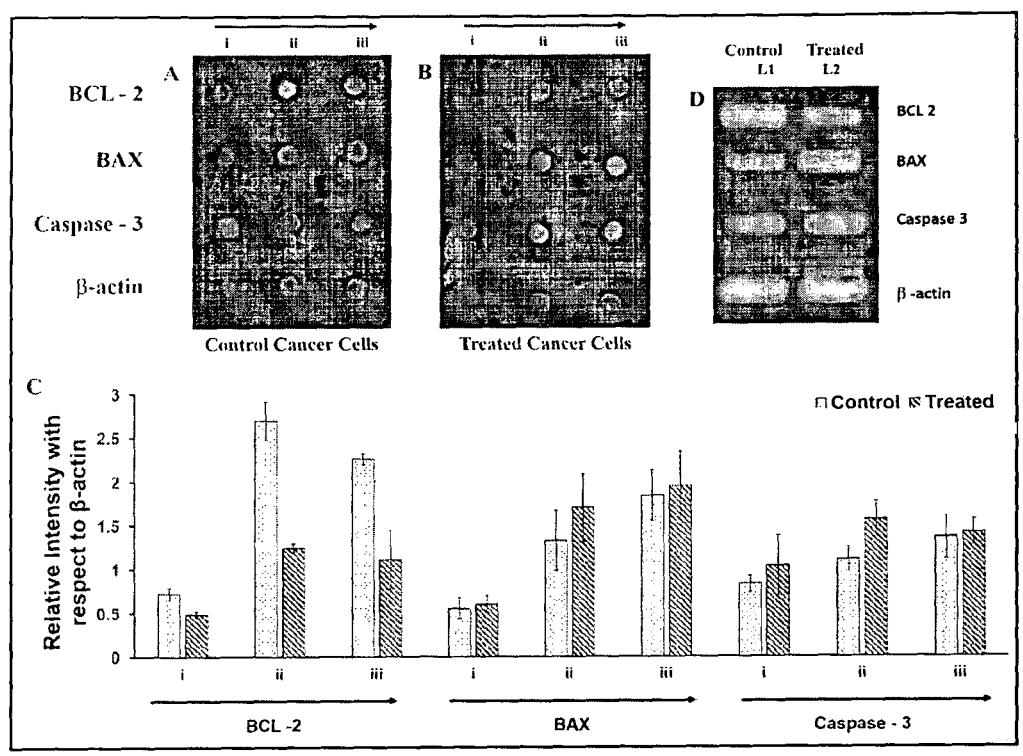

FIG. 12 illustrates A) and B) grayscale image of Gene expression levels from control and treated HeLa cells (respectively) under UV illumination analysed by array based technique with gold nanoclusters as signal generating agents. Increasing amounts (left to right in each row as indicated by the arrow) of ssDNA was immobilized on the nitrocellulose membrane for analysis ((i) 0.18 µg, (ii) 0.37 µg and (iii) 0.74 µg). Increasing amounts of PCR products from both control and treated cells were hybridized ((i) 0.18 µg, (ii) 0.37 µg and (iii) 0.74 µg). Gold nanoclusters were then synthesized on the spots of the membrane. C) Relative luminescence intensity of various genes in control and treated HeLa cells as analysed from membrane. D) Standard gel electrophoresis with EtBr staining. L1 and L2 lanes correspond to control and treated samples.

Figure 13:
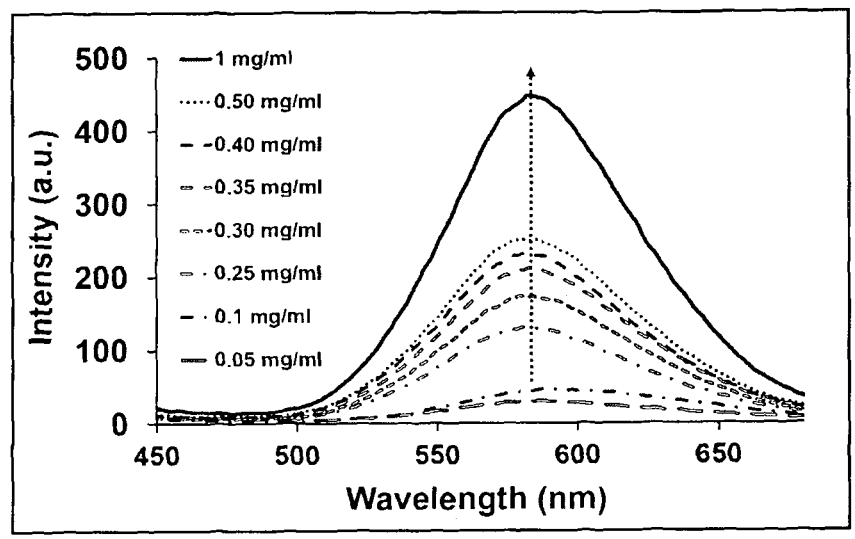

FIG. 13 illustrates synthesis of gold nanoclusters with protein BSA (Bovine Serum Albumin) as template in the liquid phase.

Figure 14:
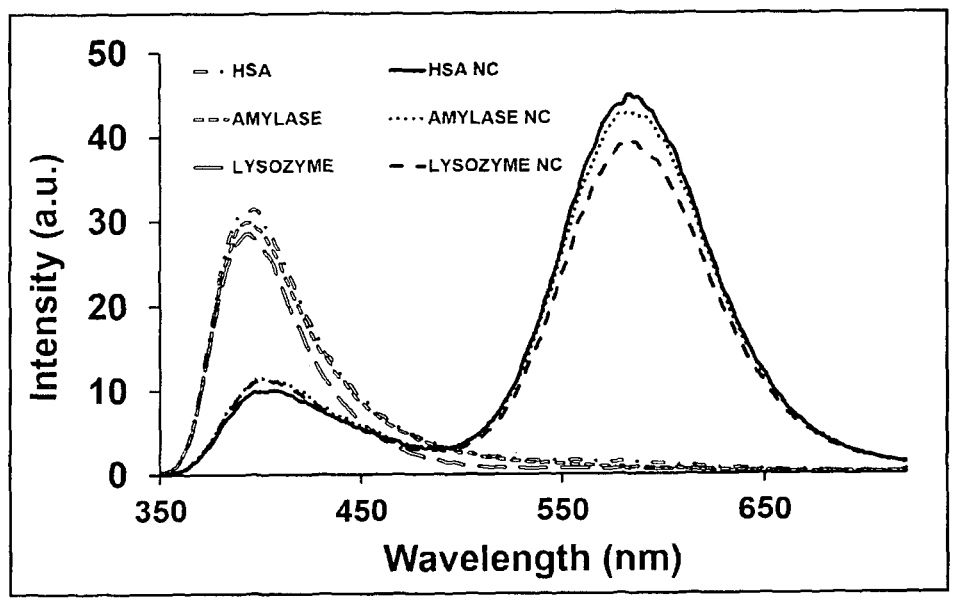

FIG. 14 illustrates synthesis of gold nanoclusters using different proteins in the liquid phase.

Figure 15:
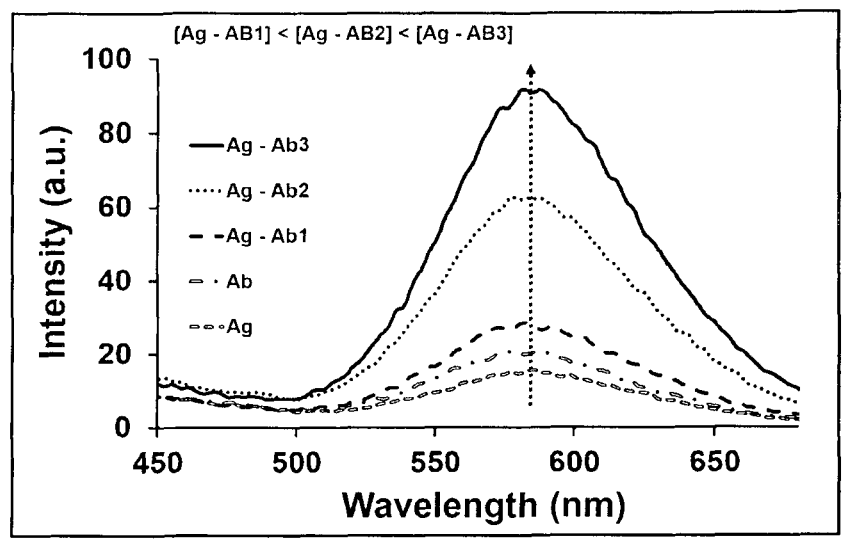

FIG. 15 illustrates probing antigen—antibody interactions with luminescence intensity of gold nanoclusters in the liquid phase.

Figure 16:
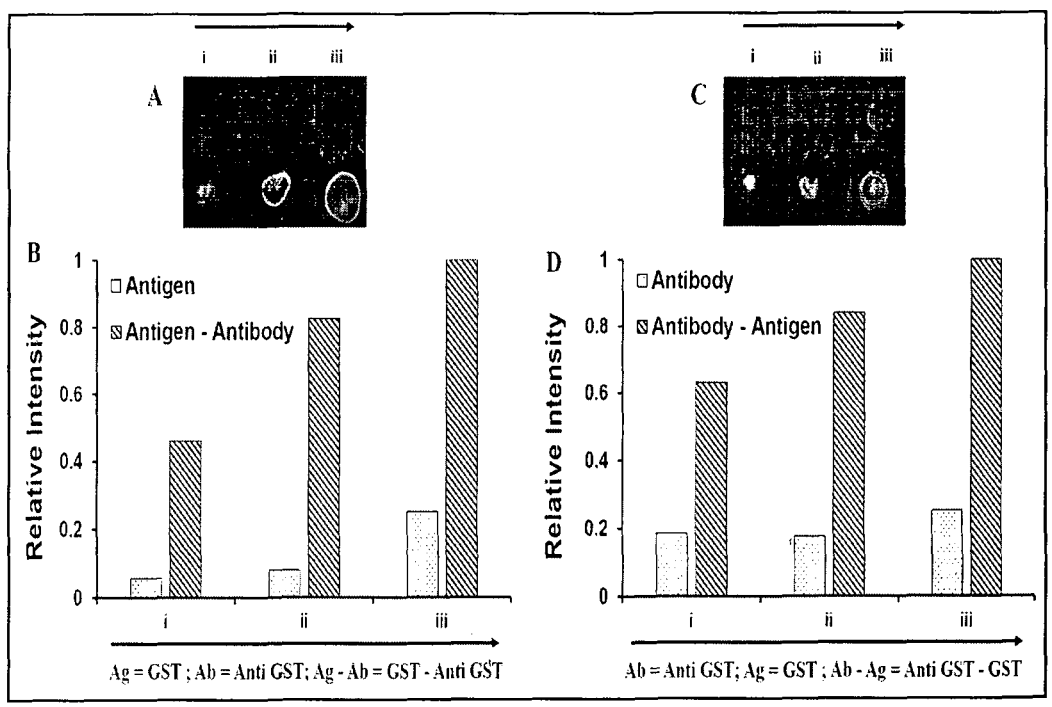

FIG. 16 illustrates probing antigen—antibody interactions with luminescence intensity of gold nanoclusters synthesized on PVDF membrane.

A) Grayscale and RGB images under UV illumination of Anti-glutathione-S-transferase (antibody) immobilized on the PVDF membrane in increasing amounts (left to right as indicated by the arrow) in two rows ((i) 0.1 µg, (ii) 0.2 µg and (iii) 0.4 µg). Then, GST (antigen) incubated in increasing amounts in only one of the rows ((i) 0.1 µg, (ii) 0.2 µg and (iii) 0.4. µg). Gold nanoclusters were then synthesized on all the spots. B) Relative intensities of various amounts of antigen and antigen-antibody as analysed from membrane, the reverse can also be done where GST antigen was initially immobilized on the membrane, followed by incubation of anti-GST as shown in C and D.

Figure 17:
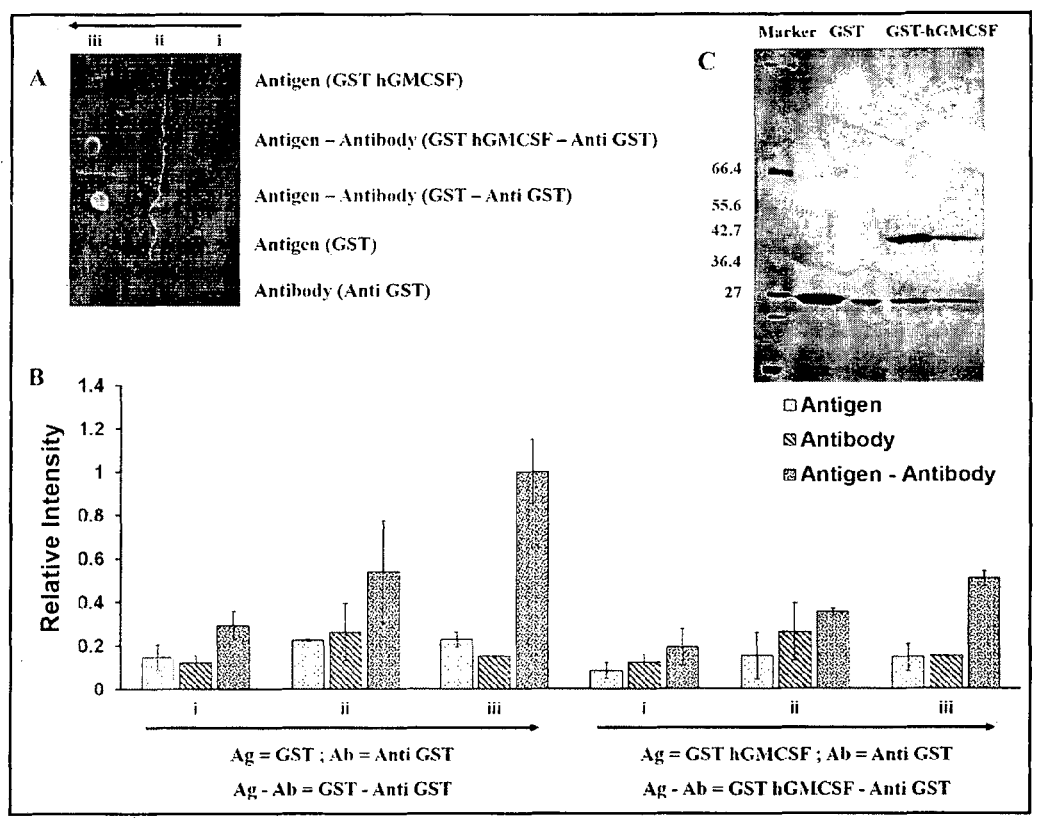

FIG. 17 illustrates Protein expression level studies with gold nanoclusters.

A) Grayscale image of the PVDF membrane under UV illumination of anti-GST antibody ((i) 0.1 µg, (ii) 0.2 µg and (iii) 0.4 µg) immobilized on to the PVDF membrane and was interacted with GST tagged hGMCSF ((i) 0.08 µg, (ii) 0.16 µg and (iii) 0.32 µg) and pure GST ((i) 0.1 µg, (ii) 0.2 µg and (iii) 0.4 µg). Increasing amounts of only GST tagged hGMCSF, pure GST and Ab (Anti-GST) were immobilized on the PVDF membrane for comparison and analysis. B) Relative luminescence intensity analysis of protein expression, C) SDS PAGE results of pure GST and GST-tagged hGMCSF.

Figure 18:
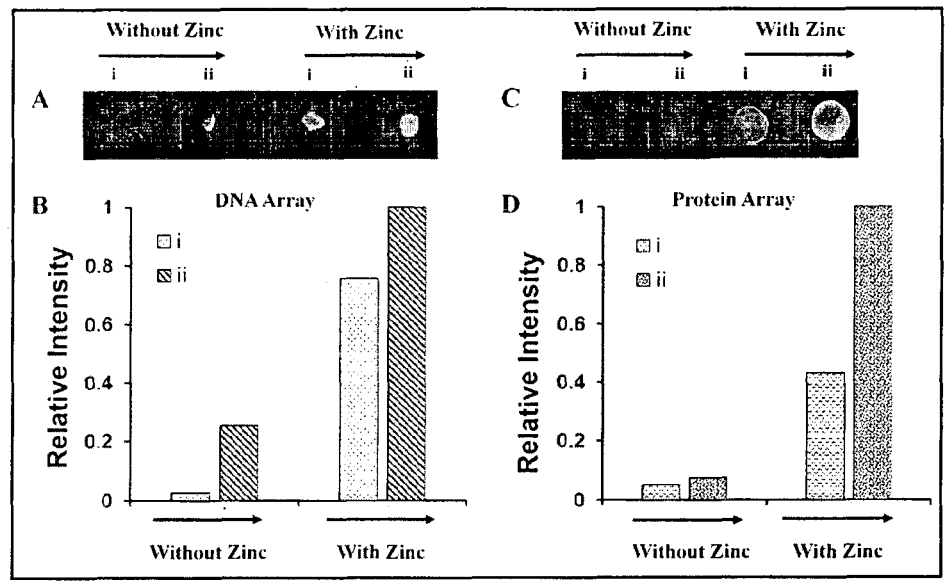

FIG. 18 represents Luminescence enhancement with zinc ions in solid phase

A, B) Grayscale images of nitrocellulose/PVDF membrane under UV illumination without and with zinc addition after gold nanocluster synthesis on dsDNA/proteins. C, D) Relative luminescence intensity analysis without and with zinc addition.

Example 1

Functional Features of Device i) Thermocycler Unit:

The hardware of the thermocycler constitutes switchable sample holders for 0.2 mL PCR tubes and a stage for placing membrane, lid with cartridge heater as heating element, two temperature sensors, heat sink with fan, Peltier element for heating and cooling, Arduino Uno based microcontroller unit, USB cable type A/B and electronic circuit. The thermocycler is controlled by a graphical user interface (GUI) coded in G language (LabVIEW).

Figure 1:
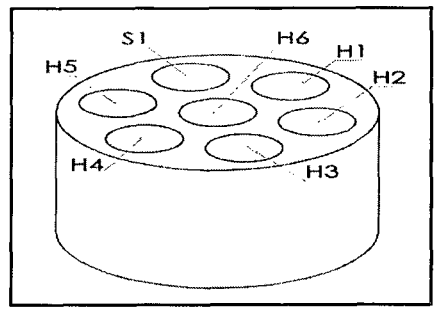
FIG. 1 illustrates structural details of the Sample Holder for 0.2 mL PCR tubes. At S1 the temperature sensor is mounted and H1 to H6 are allotted for holding the PCR tubes.

The sample holder is made of aluminium as shown in FIG. 1. It consists of 7 holes, H1 to H6 to hold the samples and S1 for the temperature sensor. The sample holder is shielded with a heat insulating material on the sides. The bottom of the holder is exposed to Peltier unit which heats and cools the sample holder. The Peltier unit is connected to the heat sink which in turn is connected to the fan. The whole assembly is held on four supports. The sample holder can achieve temperature ranging from 15° C. to 95° C.

Figure 2:
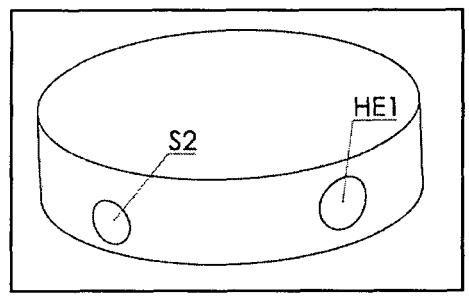
FIG. 2 illustrates structure of the Lid for 0.2 mL PCR tubes. At HE1 the heating element is placed and the temperature sensor is placed in S2.

High temperature at the top of the PCR tube is maintained in order to avoid condensation inside the tube. This is provided by an aluminium lid as shown in FIG. 2 which sits above the cap of PCR tube. The lid consists of two holes on the circumference, HE1 for the heating element to heat the lid and S2 for the temperature sensor. The lid is heated with the cartridge heating element and is positioned above the cap of PCR tubes and can achieve temperatures from room temperature to 120° C.

Figure 3:
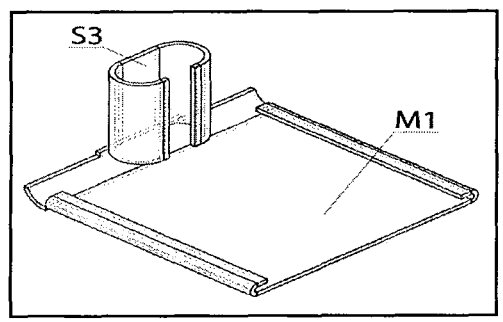
FIG. 3 illustrates the structure of the Membrane Holder Plate. Here S3 represents mounting of the temperature sensor. The membrane is to slide (placed) on the surface of the plate (M1).

Another plate with mountable temperature sensor is used to heat and cool paper based membrane (with a maximum dimensions of 40 mm×40 mm) for array based studies as shown in FIG. 3. The plate is provided with an extension S3 to mount the temperature sensor. The membrane is to slide (placed) on the surface of the plate (M1).

The switchable holders help to carry out RT-PCR and array based techniques simultaneously. Arduino Uno based microcontroller unit is used to execute various operations. The additional circuit needed for the thermocycler was designed and mounted on the Arduino Uno board. However, the microcontroller unit is controlled through a Graphical User Interface (GUI 1).

The GUI 1 for the thermocycler unit is broadly divided into three sections—Input settings, Controls and Indicators.

Input settings—In this section, a particular process can be chosen i.e., PCR or Array Based Analysis. In PCR mode, initial denaturation (on/off) with denaturation time, final extension (on/off) with extension time can be set. Number of cycles of PCR can be given. Also, the lid (on/off) can be controlled with the temperature set anywhere in between room temperature to 120° C. An additional option is included to provide the maximum timeout (in seconds) within which a process is expected to start. If the process is not started within this time, the machine shuts of automatically. Also, custom temperatures and time periods can be set.

Controls—The controls involve operations such as starting a process, halting a process and exiting the application.

Indicators—There are temperature indicators indicating the temperature of the sample holder/plate and lid continuously. The time out counter indicates the time after which the particular process is triggered. There is also an indicator which shows whether a particular phase is timed out or not. If a particular operation fails to occur within the pre-set time, the timeout indicator indicates it and the machine turns off automatically. Also, there are indicators indicating the current phase in a cycle and the number of cycles that are completed. The running time for a particular phase is also indicated.

ii) Visualization Unit

Figure 4:
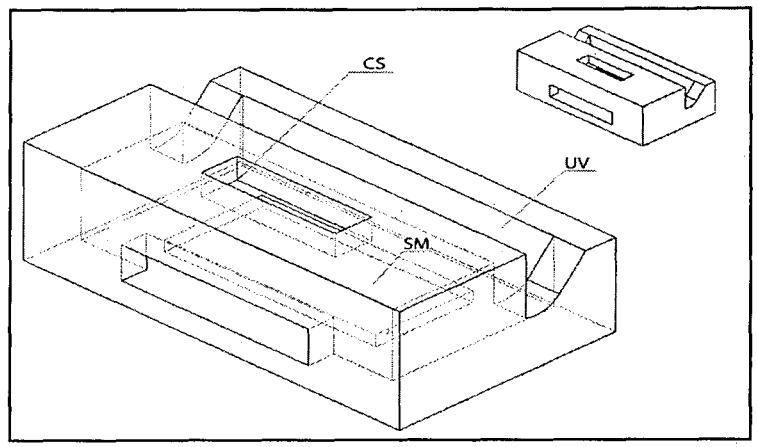
FIG. 4 represents the block diagram of the structure of the Visualization Unit equipped with an UV source (UV) consisting of interchangeable tubes (i.e., for short wavelength, mid wavelength and long wavelength UV sources). It also contains a camera source (CS) for capturing the sample of interest which is placed on the sample mount (SM) indicated in the figure.

The visualizing unit FIG. 4 consists of a sample mount (SM) on which a particular sample to be examined is placed. UV source (UV, 6W, battery operated) with interchangeable tubes (for short wavelength, mid wavelength, long wavelength) was mounted at an inclined angle to illuminate the sample area properly. Camera source (CS) with adjustable parameters (through GUI) is used to capture the image for further analysis. It is also controlled through a GUI programmed in LabVIEW. The GUI 2 is divided into three panels—Acquisition, Analysis and generating Reports.

Acquisition—The Acquisition allows the user to select the camera source and start visualizing the sample. The camera can be operated in auto mode or manual mode. In the auto mode, the camera tries to focus with the pre-set parameters. However, in the manual mode, the user is allowed to change the parameters to acquire better results. Once, the desired image is achieved, the user is allowed to capture the image for storage and further analysis.

Analysis—The analysis panel allows the user to acquire the image in 8-bit grayscale mode. There lies an option to apply a threshold to the image. The user is allowed to carry out analysis over an area of interest or along a line. Region of interests (ROIs) can be selected in different geometrical shapes (such as rectangular, square, polygon, conical or any other free hand shape) for the analysis. Histogram data, X, Y averaged pixel profile over an area, line profile on a line of interest can be obtained and also exported. Also, an option for the 3D visualization of the image with variable parameters is incorporated. Each ROI can be individually visualized with the data associated with it.

Reports—This panel allows the user to export all the information obtained in analysis, do a quick plot of the information. Also, the user can fit the points with linear regression technique and can estimate the unknown points as per the fit.

iii) Functional Correlation

Input of parameters is done through a graphical approach which allows full control of the machine and visualization of the running status and results easily. The conditions required for PCR, array based techniques and synthesis of signal generating agents are incorporated in the GUIs. Additionally, the GUIs are coded for visualization of the signal generating agents and even to carry out analysis for the acquired images. The results are plotted in the GUI and are exported. The combination of the above mentioned various processes makes the GUI a useful feature which brings the multiple processes in a common platform which is not available in commercial machines.

Different parts of the machine are constructed in a modular fashion. Switchable sample holders facilitate easy switching between PCR and array based analyses.

Figure 5:
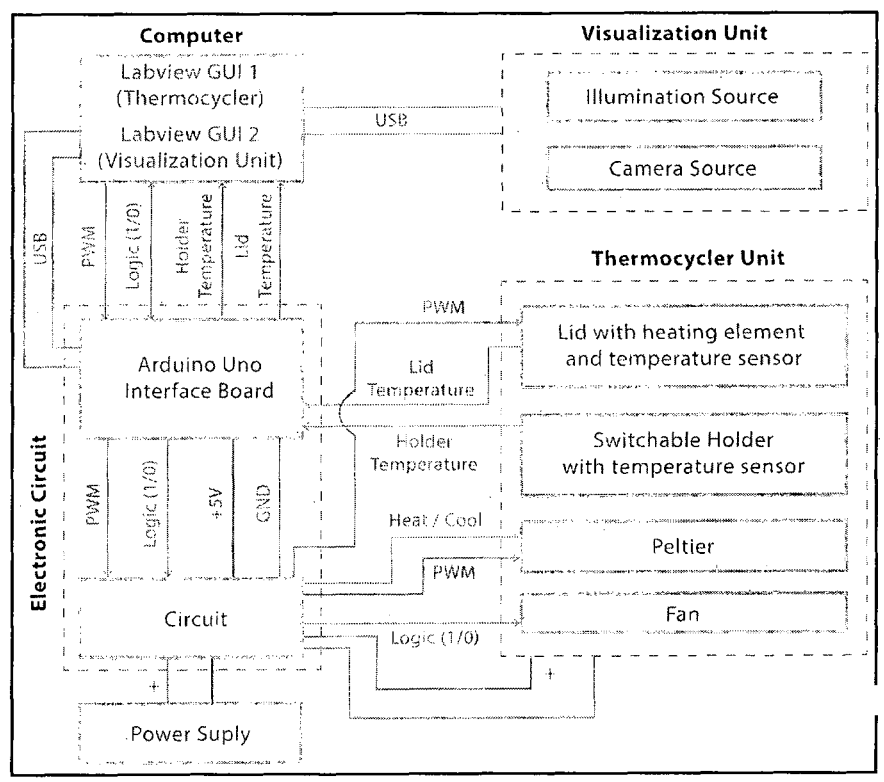
FIG. 5 represents the block diagram of different functional units of the device.

FIG. 5 explains correlation of different functional units of the complete device.

Example 2

Array Based Technique for Gene Expression Studies

Figure 6:
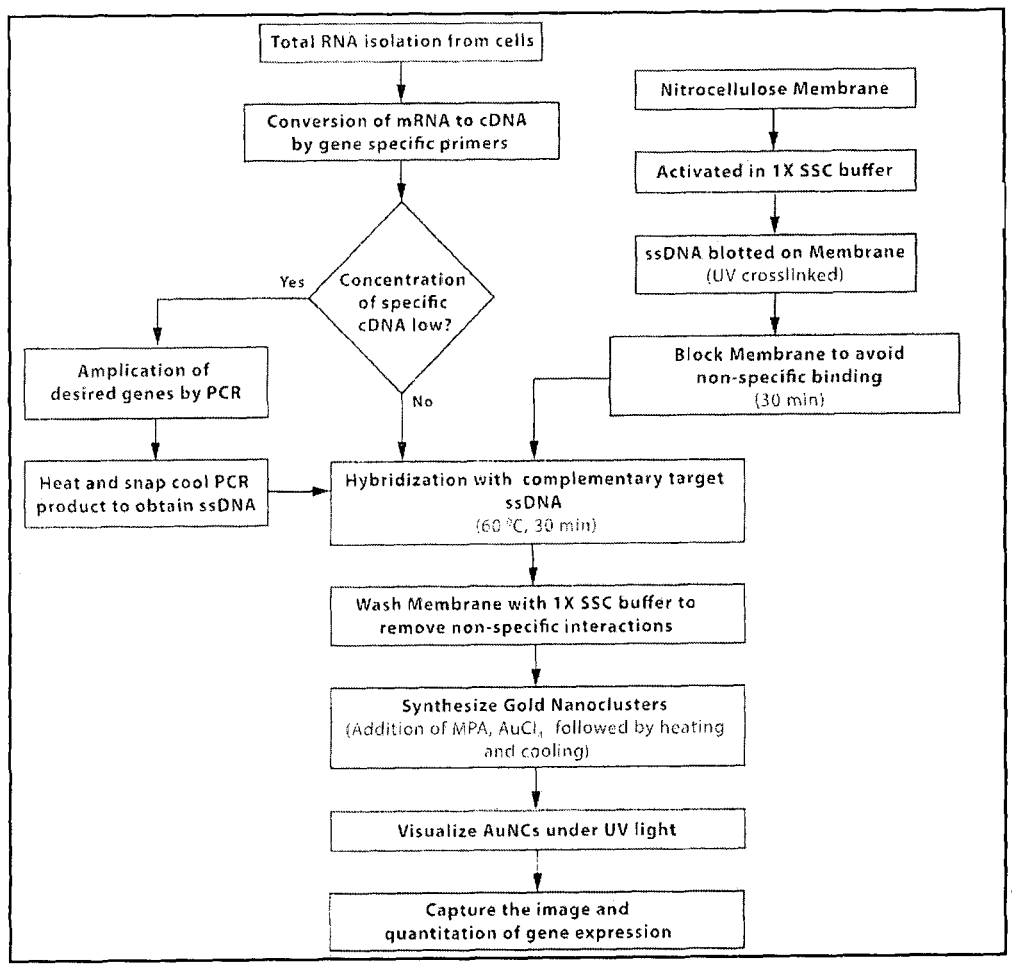
FIG. 6 represents a flow-chart of the procedure adopted for array based gene expression studies with gold nanoclusters.

For gene expression studies, the complementary ssDNA for the target gene (which is to be observed) is initially immobilized on the nitrocellulose membrane. RNA is isolated from the cells of interest. The cDNA is generated from mRNA through reverse transcription. If the cDNA is of sufficient quantity, then it is hybridized against gene specific complementary ssDNA initially immobilized on the membrane and the synthesis of the gold nanoclusters is carried out. If the quantity obtained is less, then it is amplified by the PCR process to obtain an optimum amount of target gene. The PCR product is heated and then suddenly cooled (snap-cooled). This product is then hybridized on the spots of the membrane. Gold nanoclusters are then prepared on these hybridized spots, which are then visualized under UV illumination. The image is captured and further analysed for quantization of gene expression. The layout of the steps (FIG. 6) is discussed in detail in the following sections.

Step 1: Isolation of RNA from Target Cells $1 \times 10^6$ cells (HeLa cells) were seeded on two 60 mm culture plates and incubated for 24 h at 37° C. in 5% $CO_2$. One plate of seeded cells were treated with the anti-cancer drug (doxorubicin) for 24 h. RNA was isolated from both the plates (control and treated cells) using standard RNA isolation protocol.

Step 2: Conversion of Total mRNA into cDNA

The isolated mRNA from step 1 was converted into cDNA in the constructed bench-top thermocycler (42° C. for 40 min, 95° C. for 2 min) using Verso cDNA kit using reverse transcriptase enzyme.

Step 3: Amplification of Genes of Interest Using Specific Primers

This step is necessary if the amount of cDNA from step 2 is not adequate for detection. The specific genes of interest were amplified using primers (obtained from Integrated DNA Technologies, IDT) and 2× PCR master mix until the desired cycles in the thermocycler.

Step 4: Immobilization of Oligonucleotide (ssDNA) on Nitrocellulose Membrane in an Array Pattern Commercially procured oligonucleotides were immobilized on nitrocellulose membrane by the following procedure.

Membrane (with nominal porosity of 0.45 µm) of suitable size (with maximum dimensions of 40 mm×40 mm) was cut and activated in 1× SSC buffer and was allowed to air dry. The commercial oligonucleotides were spotted in an array format and were UV-cross linked using standard procedure.

Step 5: Interaction of cDNA/Heated and Snap-cooled PCR Products (i.e. ssDNA) to the Complementary Oligonucleotides Immobilized on Nitrocellulose Membrane The cDNA obtained in step 2 (if it is of sufficient amount) or the PCR products (after subjecting to heating and sudden cooling) were hybridized to their respective immobilized complementary nucleotides by the following process.

The membrane was blocked using blocking solution for 15 min to avoid unspecific binding. The hybridization was carried out in 5× SSC buffer, 10% poly ethylene glycol (PEG) 6000 at 60° C. for half an hour. The membrane was then washed with 1× SSC (Saline-Sodium Citrate) buffer.

Step 6: Synthesis of Gold Nanoclusters on Hybridised Membrane

Gold nanoclusters were synthesized on the spots after hybridization using the following procedure. 1.5 µL of 0.7 mM $HAuCl_4$ and 0.5 µL of 0.01 M 3-mercaptopropionic acid (MPA) were added on each spot of the membrane. The membrane was then placed on the plate (with temperature sensor) which was then heated at 95° C. for 2 min and then cooled immediately to 15° C.

Step 7: Analysis of Gene Expression Based on Differential Spot Intensities on Hybridised Membrane The membrane was then visualized in the visualization unit of the machine. The membrane was placed on the sample mount (SM) in the visualization unit and was excited under UV illumination and the luminescence images were acquired. The picture was adjusted to the range of pixels desired. Then, regions of interests (ROIs) were selected. Histogram data of selected ROI were obtained. X- and Y-averaged intensity profile of the ROI, i.e.; the averaged value of the pixel values along each line vertically and horizontally were acquired. The pixel values along the selected line were also obtained through line profile graph. A comparison of the relative intensity levels of the ROIs revealed the amount of hybridized DNA and the nature of hybridization. This helps in acquiring the relative gene expression levels by various combinations and amounts of genes.

Example 3

Array Based Technique for Protein Expression Studies

Glutathione-S-transferase (GST) fusion tag based system was exploited for protein expression studies. Because GST rapidly folds into a stable and highly soluble protein upon translation, inclusion of the GST tag promotes greater expression and solubility of the recombinant proteins than expression without the tag. GST tagged proteins can be purified or detected based on the ability of the GST to bind with high affinity and specificity to its substrate glutathione.

For the detection of GST tagged protein, pure GST and GST tagged hGMCSF (human granulocyte macrophage colony stimulating factor) was taken and primary antibody specific to GST was allowed to interact with GST and GST tagged hGMCSF. Gold clusters were then synthesized on the interacted products and based on the intensity of emission of gold nanoclusters formed, the amount of protein expressed was identified.

Figure 7:
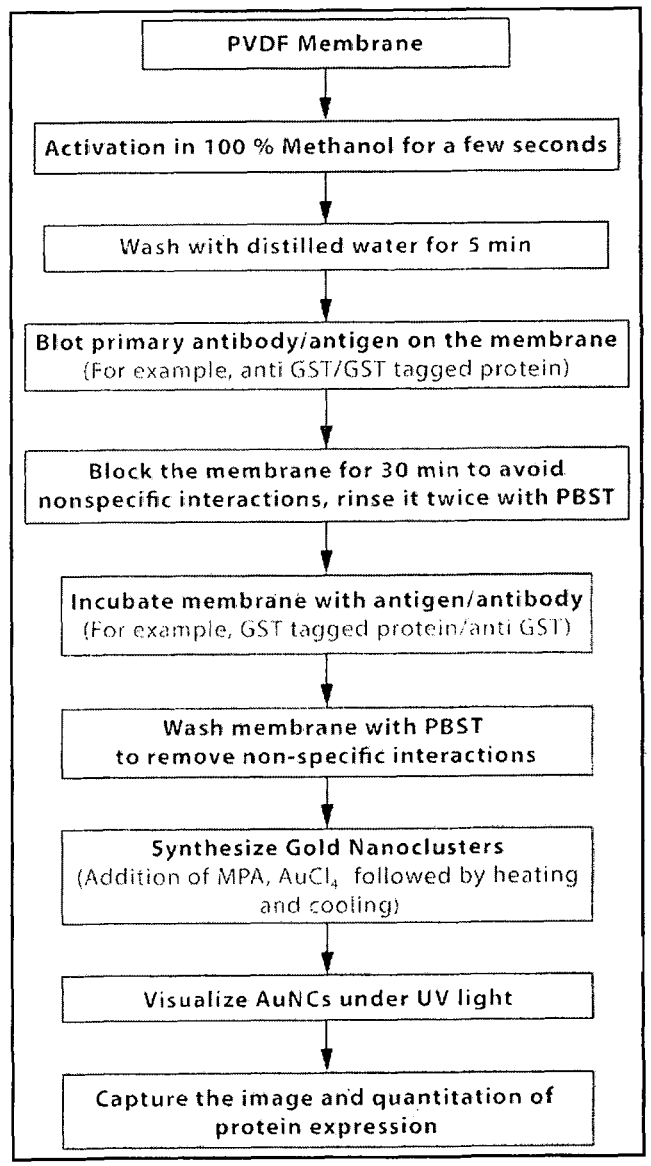
FIG. 7 represents a flow-chart of the procedure adopted for array based protein expression studies with gold nanoclusters.

The array based protein expression studies are carried on the PVDF membrane. After methanol treatment of the PVDF membrane, antibody is blotted on it. Following this, antigen is allowed to interact on the antibody blotted membrane. Gold nanoclusters are then synthesized on the membrane and are visualized under UV illumination. The image is captured and further analysed for quantization of protein expression. The detailed procedure steps for array based protein expression studies are shown in FIG. 7 and are detailed out below.

Step 1: Immobilization of Primary Antibody on PVDF Membrane in an Array Pattern

The primary antibody was immobilized on the PVDF membrane by the following procedure. Membrane of suitable size (with maximum dimensions of 40 mm×40 mm) was cut and activated in methanol. Primary antibody of different dilutions were spotted on the membrane. During spotting the membrane should not dry. The drop was placed on the membrane and was allowed to air dry for 15-20 min.

Step 2: Interaction of Antigens with Antibodies on PVDF Membrane

The membrane was blocked using blocking solution for 30 min to avoid unspecific binding. The membrane was then incubated with respective antigens for 30 min and was washed with PBST (phosphate buffered saline with Tween 20) buffer.

Step 3: Synthesis of Gold Nanocluster on PVDF Membrane

Gold nanoclusters were synthesized with proteins as templates on the spots, after antigen-antibody interaction was allowed to occur, using the following procedure. 1.5 µL of 0.7 mM $HAuCl_4$ and 0.5 µL of 0.01 M 3-mercaptopropionic acid (MPA) was added on each spot and membrane was heated at 95° C. for 2 min and then cooled to 15° C.

Step 4: Analysis of Amount of Antigen Present with Respect to Antibody Based on Differential Spot Intensities on PVDF Membrane The membrane was then visualized in the visualization unit of the machine. The membrane was excited under UV illumination and the luminescence image was acquired. The picture was adjusted to the range of pixels desired. Then, regions of interest (ROIs) were selected. Histogram data of selected ROI were obtained. X- and Y-averaged intensity profile of the ROI, i.e., the averaged value of the pixel values along each line vertically and horizontally were obtained. The pixel values along the selected line were also obtained through line profile graph. A comparison of the relative intensity levels of the ROIs reveals the information about the antigen—antibody interactions. This helps in acquiring the relative protein expression levels through various combinations of amounts of antigens and antibodies.

Example 4

Comparison of PCR Amplification with Commercial Machine

Figure 8:
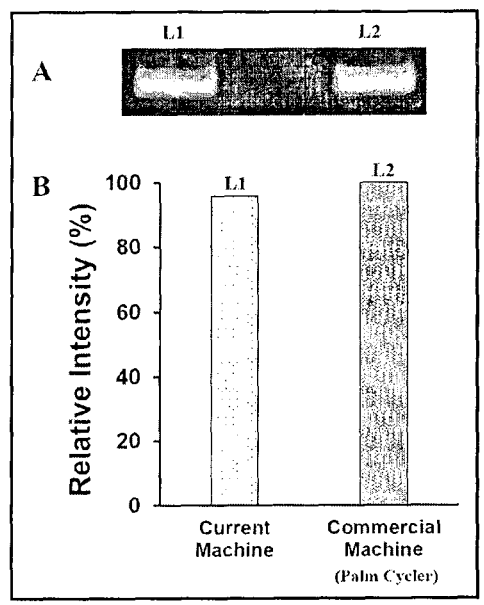
FIG. 8 illustrates comparison of the end product of PCR obtained from the device of the present invention versus that from using commercial device Here, lanes L1, L2 correspond to PCR amplicon from the proposed and commercial device respectively. A) Visualization of the gel under UV illumination. B) Relative luminescence intensity of the PCR amplicon from both the machines.

For comparison of amplification of PCR products, β-actin gene was amplified for 35 cycles using specific primers in the proposed machine as well as conventional PCR machine (Palm cycler), keeping the conditions of amplification same in both cases. The parameters used in both the cases were as follows: initial denaturation at 95° C. for 3 min followed by repeat of 95° C. for 30 sec, 55° C. for 30 sec, 72° C. for 1 min each for 35 cycles accompanied by final extension at 72° C. for 10 min. The PCR amplicons from both the machines were analysed using standard gel electrophoresis with ethidium bromide (EtBr) staining. The resultant products under UV illumination were as shown in FIG. 8. The amplification achieved was 95.85% compared to conventional PCR machine.

Example 5

Detection of Amplified Products Using Gold Nanoclusters in Liquid Phase

Figure 9:
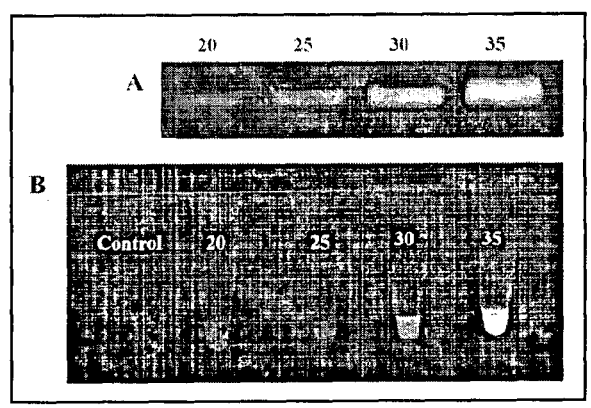
FIG. 9 describes relative quantification of PCR amplicon (β-actin) for different cycles with gold nanoclusters in the liquid phase. A) Visualization of the gel under UV illumination. B) Relative luminescence intensity of the PCR amplicon for different cycle.

For detection of amplified products using gold nanoclusters, β-actin gene was amplified for different cycles (20, 25, 30, 35) using specific primers in the proposed machine using the same parameters stated in example 4. The amplified products for different cycles were validated by a standard process of agarose gel electrophoresis and stained with EtBr for visualization. Simultaneously, another set of amplified products was taken and the synthesis of gold nanocluster was carried out on them. For synthesis, 1.0 mM $HAuCl_4$ and 0.01 M 3-mercaptopropionic acid (MPA) were added in 3:1 (v/v) ratio to the end-point PCR product (inside the PCR tube itself) and was heated at 95° C. for 2 min and then cooled to 15° C. in the machine (using PCR tube Holder), which forms the gold nanoclusters on the amplified DNA proportionately to the amplification. The luminescence intensities of the nanoclusters were used to visualize the amplified products of different cycles. A PCR tube containing PCR mixture but without cDNA was kept as the control. The PCR tubes with amplified PCR product and synthesized gold nanoclusters were placed flat on the sample mount (SM) of the visualization unit. These PCR tubes were then visualized under UV illumination (254 nm) and the images were captured with the camera unit. The amplified PCR products were successfully identified for different cycles as shown in FIG. 9. The luminescence intensity of the clusters monotonically increased with the increasing amount of PCR amplicon. For comparison, traditional gel electrophoresis (with EtBr staining) showed good agreement with the results obtained by using gold nanoclusters.

Example 6

Figure 10:
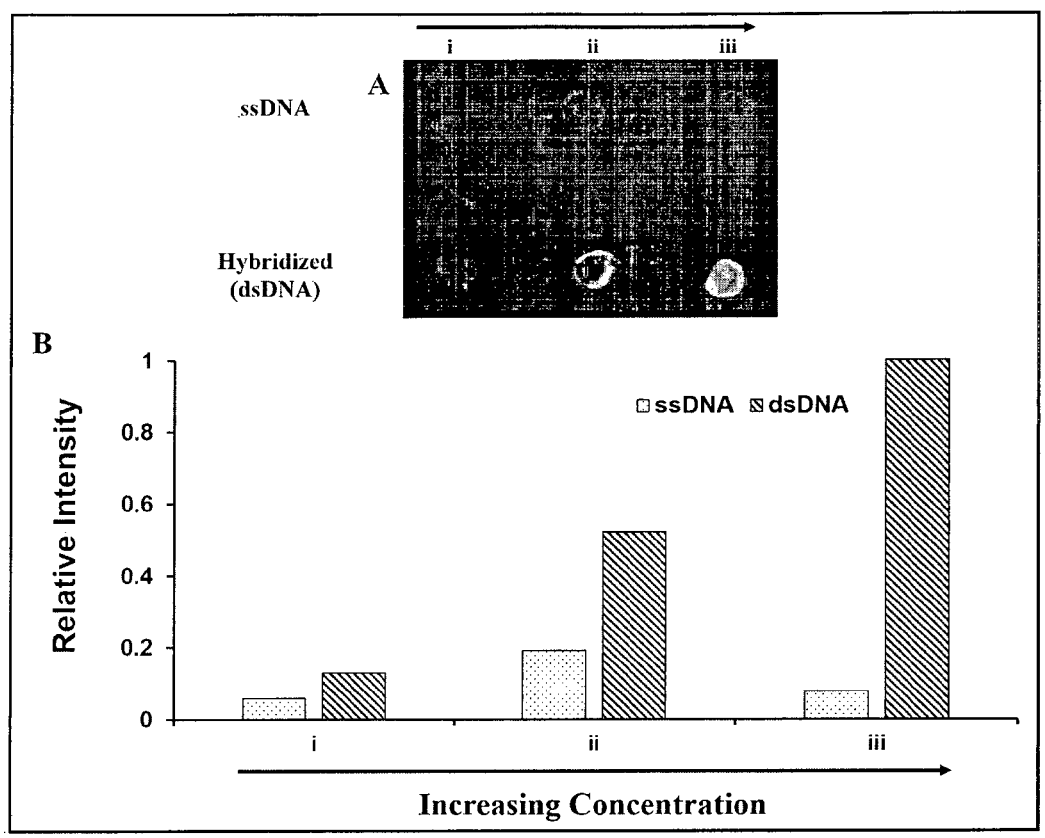
FIG. 10 represents Luminescence Intensity of gold nanoclusters synthesized on ssDNA and dsDNA both immobilized on nitrocellulose membrane.

Comparison of Luminescence Intensity of AuNCs Synthesized on ssDNA and dsDNA in Solid Phase Nitrocellulose membrane (of dimensions around 25 mm×15 mm) was activated in 1× SSC buffer and was allowed to air dry. Commercially obtained single stranded oligonucleotide (β-actin) was spotted in increasing amounts of 0.18 µg, 0.37 µg and 0.74 µg in the two rows of the array as indicated in FIG. 10 and were UV cross linked (2 min) for immobilization. The membrane was then blocked using blocking solution treatment for 15 min to avoid unspecific binding. Complementary target strands in increasing amounts of 0.18 µg, 0.37 µg and 0.74 µg were hybridized on the spots in the second row as described in Example 2. Gold nanoclusters were synthesised according to the method described in Example 2. The membrane was then washed with 1× SSC buffer and luminescence of the membrane was then visualized in the visualizing unit. It was observed that the luminescence intensity of the Au NCs increased in the hybridized dsDNA spots when compared to the control spots (i.e., single stranded oligonucleotide in row 1).

Example 7

Detection of Hybridization of Commercial Gene Sequences by Au NCs

Commercially obtained single stranded DNA of apoptotic genes (BCL—2, BAX, Caspase—3) and endogenous control β-actin were immobilized by using the same procedure as described in Example 6. Complementary target sequences were then hybridized corresponding to their single stranded counter parts using the same procedure as in Example 6. The total amount of DNA (probe+target) that was put on each spot were 0.37 µg, 0.74 µg, 1.47 µg and 2.20 µg respectively. Au NCs were then synthesized by the same process as described in earlier example and were visualized. The luminescence intensity of the hybridized DNA increased with the increasing amount in each gene as indicated in FIG. 11.

Example 8

Study of Relative Gene Expression in Control and Treated HeLa Cells

Commercially obtained single stranded DNA of apoptosis marker genes (BCL—2, BAX, Caspase—3) and endogenous control β-actin were immobilized by using the same procedure as described in Example 2 (for control array as well as treated array). The amounts of single stranded oligonucleotides used for each gene were 0.18 µg, 0.37 µg and 0.74 µg respectively. Total RNA was obtained from control and doxorubicin treated HeLa cells. cDNA was obtained from total RNA by reverse transcription. The apoptotic genes and β-actin were amplified using gene specific primers. The amplified PCR products obtained were heated and suddenly cooled (snap-cooled) before they were put on each spot in increasing amounts for hybridization corresponding to their single stranded counter parts using the same procedure as in Example 2. AuNCs were then synthesized (procedure described as in Example 2) and visualized. Simultaneously, one set of amplified PCR products of all the genes were validated by standard agarose gel electrophoresis (using ethidium bromide staining).

The relative gene expressions for each gene for different amounts were studied for control and treated cells as shown in FIG. 12. The analysis showed that apoptotic genes BAX, Caspase—3 were upregulated and BCL—2 was downregulated, signifying apoptosis in case of doxorubicin treated HeLa cells compared to the control cells. The results were in conformity with standard agarose gel electrophoresis analysis as indicated in FIG. 12D.

Example 9

Synthesis of Au NCs with Protein (BSA) as Template in Liquid Phase

Synthesis of Au NCs was carried out with increasing concentrations (0.05 mg/mL—1.0 mg/mL) of bovine serum albumin as the template with precursors HAuCl$_4$ and MPA in liquid phase.

For synthesis, 0.4 µL of 10 mM HAuCl$_4$ and 0.16 µL of 0.11 M 3-mercaptopropionic acid (MPA) were added to 20 µL of protein solution and was heated at 95° C. for 2 min and then cooled to 15° C. in the thermocycler. The luminescence spectra of the hence-formed Au NCs were then recorded using a spectrofluorimeter ($\mu_{ex}$=300 nm, $\lambda_{em}$=580 nm). The luminescence intensity of the Au NCs increased with the increasing concentration of BSA as indicated in the FIG. 13. It was observed that the luminescence intensity of the clusters increased with increase in the concentration of the protein.

Example 10

Synthesis of Au NCs with Different Proteins as Templates in Liquid Phase

The synthesis was carried on different proteins (human serum albumin, alpha amylase and lysozyme) using the same procedure as indicated in Example 9. It was observed that Au NCs were formed on all the proteins, irrespective of their class, with luminescence emission maximum at 580 nm when excited at 300 nm, as shown in FIG. 14.

Example 11

Detection of Antigen—Antibody Interaction By Synthesis of Au NCs in Liquid Phase Au NCs were synthesized on GST (glutathione S transferase) as antigen, primary anti-GST as antibody and different concentrations of GST—anti GST (Ag-Ab, after interaction) by the same process as described in Example 9. The luminescence intensity increased with the increasing concentrations of GST-anti GST (Ag-Ab) together compared to GST (Ag) and anti GST (Ab) alone as shown in FIG. 15. It was observed that the luminescence intensity of the gold nanoclusters in the antibody-antigen sample was more compared to the intensity of the clusters synthesized in the presence of antibody or antigen only Example 12

Detection of Antigen—Antibody Interaction By Au NCs in Solid Phase

Anti-GST antibody was immobilized on PVDF membrane in increasing amounts of 0.1 µg, 0.2 µg and 0.4 µg in two rows. The membrane was blocked using blocking solution for 30 min to avoid unspecific binding. The membrane was then incubated with GST antigen for 30 min in amounts of 0.1 µg, 0.2 µg and 0.4 µg in only one row (three spots). The membrane was then washed with PBST buffer to remove unreacted products.

Au NCs were then synthesized on each spot of the membrane. For Au NC synthesis, 1.5 µL of 0.7 mM HAuCl$_4$ and 0.5 µL of 0.01 M 3-mercaptopropionic acid (MPA) were added on each spot and the membrane was heated at 95° C. for 2 min and then cooled to 15° C. in the plate with the thermocycler. The luminescence intensity of the spots with GST—anti GST antibody was higher compared to the anti-GST antibody alone as shown in FIG. 16A, B. It was observed that the luminescence intensity of the gold nanoclusters in the antibody—antigen sample was more compared to the intensity of the clusters on antibody only.

However, instead of immobilizing anti-GST antibody, the reverse can also be done where GST antigen is initially immobilized on the membrane, followed by incubation of anti-GST in a similar manner described above. The results are shown in FIG. 16C, D.

Example 13

Study of Protein Expression Using Au NCs

GST tagged human granulocyte macrophage colony stimulating factor (hGMCSF) was cloned and expressed along with pure GST as control. Anti-GST antibody was immobilized on to the PVDF membrane and was interacted with GST tagged hGMCSF and GST in similar process as described in Example 12. Increasing amount of only GST tagged hGMCSF and only GST, anti-GST antibody only were also immobilised for comparison. The final amount of GST tagged hGMCSF were 0.08 µg, 0.16 µg and 0.32 µg; GST tagged hGMCSF-anti-GST were 0.18 µg, 0.36 µg and 0.72 µg; GST were 0.1 µg, 0.2 µg and 0.4 µg; GST—Anti GST were 0.2 µg, 0.4 µg and 0.8 µg; anti-GST were 0.1 µg, 0.2 µg and 0.4 µg.

Au NCs were synthesized by the same process as described in Example 12 and were visualized under UV illumination. The relative luminescence intensity was higher in case of GST compared to GST tagged hGMCSF. By this we can infer that the GST tag was intact in case of GST tagged hGMCSF with the help of which its expression can be studied relatively with pure GST as control. The results were in accordance with standard SDS PAGE (sodium dodecyl sulphate polyacrylamide gel electrophoresis) results as shown in FIG. 17C.

Example 14

Luminescence Enhancement with Zinc Ions in Solid Phase

Increasing amounts of DNA ((i) 0.37 µg, (ii) 0.74 µg)/Antibody ((i) 0.1 µg, (ii) 0.74 µg) were spotted on to nitrocellulose/PVDF membrane in two sets. Complementary DNA ((i) 0.37 µg, (ii) 1.1 µg)/Antigen((i) 0.1 µg, (ii) 0.4 µg) was interacted and Au NCs were synthesized on all the spots as described in earlier experiments. In one of the rows, zinc ions (5 µg/µL) were added during synthesis. The luminescence intensity was found to be increased in cases where zinc ions were added as shown in FIG. 18. Hence, this technique can be used for enhancement of luminescence in the membrane in case of lower signal intensity.

Hence, the present invention provides a user-friendly device with integrated methods to carry out both RT-PCR and array based techniques along with the detection and visualization of the products and subsequent analysis of the results. The detection is achieved through a quick synthesis of gold nanoclusters directly on the biomolecules as template in the device itself, visualization of the same under UV illumination and capturing the image with a camera.

We claim:

1. A device for carrying out reverse transcription polymerase chain reaction (RT-PCR) and/or array based analysis, comprising:

i) a thermocycler unit;
wherein the thermocycler unit comprises switchable sample holders comprising (a) a PCR tube holder to hold PCR tubes with a lid having a heating element and a temperature sensor and (b) a membrane holder stage for supporting a membrane for said array based analysis and having a temperature sensor;
wherein the thermocycler unit comprises heating and cooling elements for subjecting said PCR tube holder or said membrane holder stage to heating and cooling cycles for RT-PCR and/or array based analysis with gold nanoclusters as a signal generating luminescent agent on any of said switchable sample holders; and
wherein the thermocycler unit provides for in-situ synthesis of said gold nanoclusters as a signal generating luminescent agents on reverse transcription polymerase chain reacted sample in said PCR tubes on said PCR tube holder or in array based membrane on said membrane holder stage;
a fan;
a heat sink;
wherein said heating and cooling elements are connected to said fan and said heat sink to heat/cool the (a) said PCR tube holder along with lid with heating element, temperature sensors for monitoring temperatures of the PCR tube holder and lid of the PCR tubes having said heating elements or (b) said membrane holder stage;

ii) a visualization unit comprising:
a UV light source for visualization of said RT-PCR reacted sample products or array based membrane with said gold nanoclusters as a signal generating luminescent agents in said PCR Tubes or array based membrane;
Web-camera to capture image of said RT-PCR reacted sample products or array based membrane with said gold nanoclusters as a signal generating luminescent agents in said PCR Tubes or array based membrane;
a computer (PC) and microcontroller unit controlled through a GUI (Graphical User Interface);
said thermocycler unit and said visualization unit interfaced to said computer (PC) and microcontroller unit controlled through GUI (Graphical User Interface) for carrying out said reverse transcription polymerase chain reaction (RT-PCR) and/or array based analysis based on detection of increase in luminescence intensity of the said gold nonoclusters as a signal generating luminescent agents monotonically with the concentration of dsDNA or amount of protein based on the reverse transcription polymerase chain reacted samples or array based membrane.

2. The device as claimed in claim 1 wherein said heating and cooling elements comprise a peltier element.

3. The device of claim 1 wherein said UV light source is configured to provide 254 nanometer wavelength light.

* * * * *

SEQUENCE LISTING

```
<160> NUMBER OF SEQ ID NOS: 16

<210> SEQ ID NO 1
<211> LENGTH: 60
<212> TYPE: DNA
<213> ORGANISM: Artificial Sequence
<220> FEATURE:
<223> OTHER INFORMATION: ssDNA sequence of beta-actin

<400> SEQUENCE: 1
caccatggat gatgatatcg ccgcgctcgt cgtcgacaac ggctccggca tgtgcaaggc    60

<210> SEQ ID NO 2
<211> LENGTH: 60
<212> TYPE: DNA
<213> ORGANISM: Artificial Sequence
<220> FEATURE:
<223> OTHER INFORMATION: Complementary ssDNA sequence of beta-actin

<400> SEQUENCE: 2
gtggtaccta ctactatagc ggcgcgagca gcagctgttg ccgaggccgt acacgttccg    60

<210> SEQ ID NO 3
<211> LENGTH: 50
<212> TYPE: DNA
<213> ORGANISM: Artificial Sequence
<220> FEATURE:
<223> OTHER INFORMATION: ssDNA sequence of BCL2

<400> SEQUENCE: 3
gcttttcctc tgggaaggat ggcgcacgct gggagaacag ggtacgataa    50

<210> SEQ ID NO 4
<211> LENGTH: 50
<212> TYPE: DNA
<213> ORGANISM: Artificial Sequence
```

```
<220> FEATURE:
<223> OTHER INFORMATION: Complementary ssDNA sequence of BCL2

<400> SEQUENCE: 4
cgaaaaggag acccttccta ccgcgtgcga ccctcttgtc ccatgctatt           50

<210> SEQ ID NO 5
<211> LENGTH: 44
<212> TYPE: DNA
<213> ORGANISM: Artificial Sequence
<220> FEATURE:
<223> OTHER INFORMATION: ssDNA sequence of BAX

<400> SEQUENCE: 5
cggcgggagc ggcggtgatg gacgggtccg gggagcagcc caga                44

<210> SEQ ID NO 6
<211> LENGTH: 44
<212> TYPE: DNA
<213> ORGANISM: Artificial Sequence
<220> FEATURE:
<223> OTHER INFORMATION: Complementary ssDNA sequence of BAX

<400> SEQUENCE: 6
gccgccctcg ccgccactac ctgcccaggc ccctcgtcgg gtct                44

<210> SEQ ID NO 7
<211> LENGTH: 47
<212> TYPE: DNA
<213> ORGANISM: Artificial Sequence
<220> FEATURE:
<223> OTHER INFORMATION: ssDNA sequence of Caspase3

<400> SEQUENCE: 7
aataaaggta tccatggaga acactgaaaa ctcagtggat tcaaaat             47

<210> SEQ ID NO 8
<211> LENGTH: 47
<212> TYPE: DNA
<213> ORGANISM: Artificial Sequence
<220> FEATURE:
<223> OTHER INFORMATION: Complementary ssDNA sequence of Caspase3

<400> SEQUENCE: 8
ttatttccat aggtacctct tgtgactttt gagtcaccta agtttta             47

<210> SEQ ID NO 9
<211> LENGTH: 20
<212> TYPE: DNA
<213> ORGANISM: Artificial Sequence
<220> FEATURE:
<223> OTHER INFORMATION: Sequence of the forward primer for beta-actin

<400> SEQUENCE: 9
ctgtctggcg gcaccaccat                                           20

<210> SEQ ID NO 10
<211> LENGTH: 20
<212> TYPE: DNA
<213> ORGANISM: Artificial Sequence
<220> FEATURE:
<223> OTHER INFORMATION: Sequence of the reverse primer for beta-actin

<400> SEQUENCE: 10
gcaactaagt catagtccgc                                           20
```

```
<210> SEQ ID NO 11
<211> LENGTH: 29
<212> TYPE: DNA
<213> ORGANISM: Artificial Sequence
<220> FEATURE:
<223> OTHER INFORMATION: Sequence of the forward primer for BCL2

<400> SEQUENCE: 11
agatgtccag ccagccagct gcacctgac                                    29

<210> SEQ ID NO 12
<211> LENGTH: 27
<212> TYPE: DNA
<213> ORGANISM: Artificial Sequence
<220> FEATURE:
<223> OTHER INFORMATION: Sequence of the reverse primer for BCL2

<400> SEQUENCE: 12
agataggcac ccagggtgat gcaagct                                      27

<210> SEQ ID NO 13
<211> LENGTH: 24
<212> TYPE: DNA
<213> ORGANISM: Artificial Sequence
<220> FEATURE:
<223> OTHER INFORMATION: Sequence of the forward primer for BAX

<400> SEQUENCE: 13
aagctgagcg agtgtctcaa gcgc                                         24

<210> SEQ ID NO 14
<211> LENGTH: 22
<212> TYPE: DNA
<213> ORGANISM: Artificial Sequence
<220> FEATURE:
<223> OTHER INFORMATION: Sequence of the reverse primer for BAX

<400> SEQUENCE: 14
tcccgccaca aagatggtca cg                                           22

<210> SEQ ID NO 15
<211> LENGTH: 22
<212> TYPE: DNA
<213> ORGANISM: Artificial Sequence
<220> FEATURE:
<223> OTHER INFORMATION: Sequence of the forward primer for Caspase3

<400> SEQUENCE: 15
tttgtttgtg tgcttctgag cc                                           22

<210> SEQ ID NO 16
<211> LENGTH: 20
<212> TYPE: DNA
<213> ORGANISM: Artificial Sequence
<220> FEATURE:
<223> OTHER INFORMATION: Sequence of the reverse primer for Caspase3

<400> SEQUENCE: 16
attctgttgc cacctttcgg                                              20
```